United States Patent
Okumoto et al.

(10) Patent No.: US 8,043,560 B2
(45) Date of Patent: Oct. 25, 2011

(54) AUTOMATIC ANALYZER

(75) Inventors: Keiji Okumoto, Nishinomiya (JP);
Masahiko Takahara, Nishinomiya (JP);
Yoshifumi Okajima, Nishinomiya (JP)

(73) Assignee: Furuno Electric Co., Ltd., Nishinomiya (JP)

( * ) Notice: Subject to any disclaimer, the term of this patent is extended or adjusted under 35 U.S.C. 154(b) by 1037 days.

(21) Appl. No.: 11/826,761

(22) Filed: Jul. 18, 2007

(65) Prior Publication Data
US 2008/0019868 A1    Jan. 24, 2008

(30) Foreign Application Priority Data
Jul. 19, 2006    (JP) ................................ 2006-196545

(51) Int. Cl.
*G01N 21/00*    (2006.01)
(52) U.S. Cl. ................ 422/64; 422/50; 422/63; 422/65; 422/400; 422/82.01; 422/82.05; 436/180
(58) Field of Classification Search .............. 422/63–65, 422/50, 400, 82.01, 82.05; 436/180
See application file for complete search history.

(56) References Cited

U.S. PATENT DOCUMENTS

| | | | | |
|---|---|---|---|---|
| 4,313,735 A | * | 2/1982 | Yamashita et al. | 436/47 |
| 4,539,296 A | | 9/1985 | Manabe | |
| 5,380,487 A | * | 1/1995 | Choperena et al. | 422/63 |

FOREIGN PATENT DOCUMENTS

JP    3035601 B2    2/2000

* cited by examiner

*Primary Examiner* — Jyoti Nagpaul
(74) *Attorney, Agent, or Firm* — Birch, Stewart, Kolasch & Birch, LLP

(57) ABSTRACT

An automatic analyzer using a reaction vessels of disposable type is provided which is compact in construction and with high accuracy of measurement.

The analyzer is comprised with a reaction container which is capable of having a plurality of cuvettes of disposable type set therein, an extracting and injecting unit for injecting a first reagent, a specimen and a second reagent into a disposable cuvette, a light measuring unit for emitting light to the cuvette, and for measuring absorbance thereof and a CPU for producing a calculated value based on outputs of the light measuring unit.

The light measuring unit measures absorbance of the first reagent, specimen and second reagent injected into and reacted with each other in a disposable cuvette, and also measures an air blank value representing absorbance of an empty disposable cuvette and a first reagent blank value representing absorbance of a disposable cuvette having first reagent in the cuvette (S104, S106). The CPU compensates the absorbance based on at least one of the air blank value and the first reagent blank value (S112, S113).

8 Claims, 8 Drawing Sheets

AUTOMATIC ANALYZER

CROSS REFERENCE OF RELATED APPLICATION

Japanese Patent Application Tokugan No. 2006-196545 is hereby incorporated by reference.

FIELD OF THE INVENTION

The present invention relates to an automatic analyzer for causing a specimen to react with a reagent in a reaction vessel and measuring absorbance thereof.

BACKGROUND

With Japanese Patent No. 3035601, there is mentioned a problem for an automatic analyzer of disposable type that although the apparatus is simplified in terms of construction and cost for manufacturing the apparatus is reduced, it has problems as high running cost and inefficient resource savings.

Japanese Patent No. 3035601 proposes the following construction to solve the problem. Absorbance of a dried reaction vessel without a specimen contained therein is measured by a light measuring apparatus. If an absorbance value obtained by the measurement is not within a predetermined range having an upper limit value and a lower limit value, the apparatus is controlled not to inject a specimen into the reaction vessel.

An apparatus disclosed in Japanese Patent No. 3035601 measures absorbance, i.e., so-called air blank value or a cuvette blank value of an empty vessel. If the absorbance value is not within the predetermined range, a specimen is not injected into the vessel, as explained above. Thus, it can prevent a vessel from receiving a specimen and making a measurement, with the container having been not washed and been contaminated. It has been said that resultant accuracy of measurement is increased.

It has also been said that the construction of the analyzer can be greatly simplified, since a washing device is not required thereby.

But, it is to be noted that with the apparatus disclosed in Japanese Patent No. 3035601, reaction vessels are washed after their uses by a washing device installed outside of the apparatus. Thus, the washing of reaction vessels will be burdensome. Further, a cost to clean reaction vessels for reuse will be high. Particularly, a cost of the pure water required for the washing becomes considerably high in certain countries and in areas. Thus, with the apparatus disclosed in Japanese patent No. 3035601, improvements should be made from viewpoints of washing reaction vessels and of reducing amounts of pure water to be used.

SUMMARY OF THE INVENTION

Accordingly, an object of the present invention is to provide an automatic analyzer with a high accuracy of measurement by taking an advantage of using reaction vessels of disposable type which do not need washing thereof.

Another object of the invention is to provide an automatic analyzer compactly constructed as will be explained hereinafter.

According to one aspect of the present invention, an automatic analyzer comprises a reaction container having a plurality of disposable reaction vessels set therein, a reagent injecting unit for injecting a reagent into the disposable reaction vessel, a specimen injecting unit for injecting a specimen into the disposable reaction vessel, an absorbance measuring unit for emitting light to the disposable reaction vessel and measuring absorbance thereof and an arithmetic unit for calculating based on outputs of the absorbance measuring unit. The absorbance measuring unit is constructed to measure reaction absorbance of the disposable reaction vessel having a reagent and a specimen injected therein and reacted with each other, and also measure at least one of a first blank value representing absorbance of the disposable reaction vessel which is empty and a second blank value representing absorbance of the disposable reaction vessel having only a reagent injected thereinto. The arithmetic unit is capable of making a calculation to compensate the reaction absorbance based on at least one of the first blank value and the second blank value. With this arrangement, it will be possible for the automatic analyzer using reaction vessels of disposable type to compensate an reaction absorbance based on the first blank value and the second blank value, which will enable one to obtain absorbance with small variations and with high accuracy.

As compared with a method using a so-called water blank value, there can be reduced workloads for supplying and draining pure water and also an amount of pure water used. Thus, running cost for the apparatus can be reduced.

According to another aspect of the invention, the absorbance measurement unit is constructed to measure both the first blank value and the second blank value. A designation unit is provided to select one of the first blank value and the second blank value to be used as a blank value in compensating the reaction absorbance in the arithmetic unit. With this arrangement, there can be selectively used the first blank value or the second blank value for compensating an absorbance depending on conditions.

Thus, by an appropriately selecting a compensation method, it is possible to further improve accuracy of absorbance measurements.

According to another aspect of the invention, with the automatic analyzer, the designation unit to is adapted to have an instruction that the arithmetic unit does not perform a calculation to compensate the reaction absorbance. With this arrangement, there can be flexibly obtained absorbance in response to various kinds of conditions.

According to another aspect of the invention, the automatic analyzer is comprised with a waste vessel storage unit for storing used waste disposable reaction vessel, a transport unit for removing from the reaction container a disposable reaction vessel after absorbance thereof is measured and dropping the vessel into the waste vessel storage unit, and a control unit controlling the transport unit. With this arrangement, it will be possible to provide an automatic analyzer with a high accuracy of measurement using reaction vessel of disposable which do not need washing thereof and an external device for disposal installed outside of the automatic analyzer.

According to another aspect of the invention, the automatic analyzer is comprised with a waste vessel storage unit for storing waste disposable reaction vessels, a transport unit for removing from the reaction container a disposable reaction vessel after reaction absorbance thereof is measured and dropping the vessel into the waste vessel storage unit, and a control unit controlling the transport unit, and a memory unit for memorizing the number of the waste disposable reaction vessels thrown away by the transport unit. The waste vessel storage unit is provided with a storage container mountable in and demountable from the main body and a demount sensor for detecting that the storage container is removed from the main body of the analyzer. The control unit increases its count by one each time a used waste disposable reaction vessel is thrown away by the transport unit into the waste vessel storage unit and memorizing a resultant count in the memory unit and provides a user with an alarm at a time instant when the count reaches a predetermined count value. The control unit resets the memory content in the memory unit when the demount sensor detects that the storage container is removed from the main body. With this arrangement, there is appropriately and correctly provided to a user an alarm that the storage container is becoming full.

As compared to a method, for instance, directly detecting an amount of accumulation of disposable reaction vessels, there are no false detections and it can be constructed at a low cost. Further, since the number of waste disposable reaction vessels memorized in the memory unit is automatically reset when the storage container is removed from the main body by a user, no special resetting operations are required and thus, a user's work amount will be reduced.

According to another aspect of the invention, the automatic analyzer is further comprised with a waste vessel storage unit for storing used waste disposable reaction vessels and a specimen storage unit and second specimen storage unit for storing specimens. The second specimen storage unit is provided with a holder which is slidably movable, with the holder receiving the specimen container set therein when the holder is drawn out of the main body and being pushed into and set in the main body so that a specimen can be injected by the specimen injecting unit. It is arranged that a measurement for a specimen in the second specimen storage unit can be made interruptedly during measurements for the specimens in the specimen container are being conducted. With this arrangement, when an extraordinary or urgent measurement becomes necessary while a normal analyzing measurement is being conducted, a special unexpected measurement can be performed uninterruptedly without stopping the operation of the apparatus by merely setting the specimen container having a specimen therein in the second specimen storage unit holding unit. Thus, a flexible measurement scheduling becomes possible and a high efficiency of measurement can be well maintained.

According to another aspect of the invention, an automatic analyzer comprises a storage container disposed on one side in a horizontal space in the main body of the analyzer, a container having a plurality of empty disposable reaction vessels held therein and disposed on the other side in the horizontal space, a reaction vessel turn-table having at least one disposable reaction vessel and disposed below said container, a transport unit moving three-dimensionally to pick up an empty disposable reaction vessel in said container, carry and set it at a position in the reaction vessel turn-table, a reagent storage unit having a plurality of reagent containers, in said storage container, a specimen storage unit having a plurality of specimen containers, in said storage container, a reagent extracting and injecting unit for extracting a reagent from a reagent container and injecting a quantity of the reagent into the disposable reaction vessel, a specimen extracting and injecting unit for extracting a specimen from a reagent container and injecting a quantity of the specimen into the reaction vessel, and an absorbance measuring unit for emitting light to the disposable reaction vessel and measuring absorbance thereof.

According to further aspect of the invention, the automatic analyzer further comprises a waste vessel storage unit for storing used waste disposable reaction vessels and a specimen storage unit and second specimen storage unit for storing a specimen, the second specimen storage unit provided with a holder which is slidably movable, with the holder receiving the specimen container set therein when the holder is drawn out of the main body and being pushed into and set in the main body so that a specimen can be injected by the specimen injecting unit and thus a measurement for a specimen in the second specimen storage unit can be made interruptedly during a measurements for the specimen in the specimen storage unit is being normally conducted.

According to one aspect of the present invention, an automatic analyzer comprises a reaction container having a plurality of disposable reaction vessel set therein, a reagent injecting unit for injecting a reagent into the disposable reaction vessel, a specimen injecting unit for injecting a specimen into the disposable reaction vessel, an absorbance measuring unit for emitting light to the disposable reaction vessel and measuring absorbance thereof and an arithmetic unit for calculating based on outputs of the absorbance measuring unit. The absorbance measuring unit is constructed to measure reaction absorbance of the disposable reaction vessel having a reagent and a specimen injected therein and reacted with each other, and also measure a blank value representing absorbance of the disposable reaction vessel which is empty. The arithmetic unit is capable of making a calculation to compensate the reaction absorbance based on the blank value. With this arrangement, it will be possible for the automatic analyzer using reaction vessels of disposable type to compensate a reaction absorbance based on the blank value, which will enable one to obtain absorbance with small variations and with high accuracy.

As compared with a method using a so-called water blank value, there can be reduced workloads for supplying and draining pure water and also an amount of pure water used. Thus, running cost for the apparatus can be reduced.

DETAILED DESCRIPTION OF PREFERRED EMBODIMENTS

Figure 1:
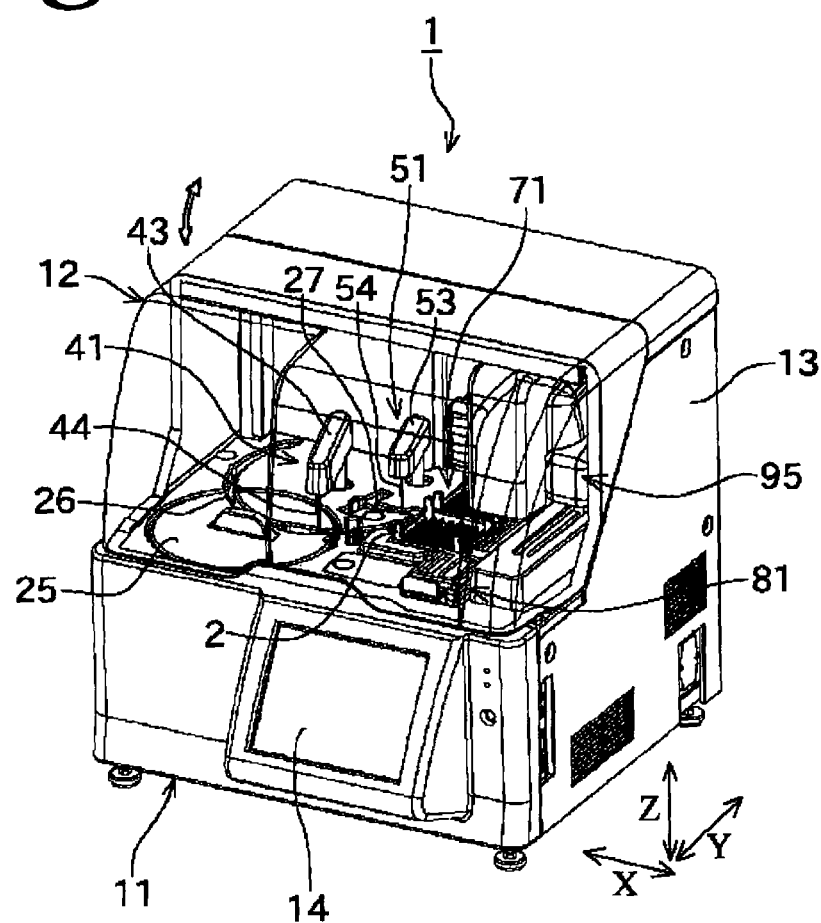
FIG. 1 is a perspective view of an embodiment of an automatic analyzer according to the present invention.

FIG. 1 shows a perspective view of an embodiment of an automatic analyzer 1 according to the present invention. The automatic analyzer 1 is used to measure ingredient densities of specimens such as blood or urine.

The automatic analyzer 1 is provided with a main body 11 and a cover 12 over an upper space above an upper surface of the main body 11. A cover support member 13 is extended upwardly from the main body 11. The cover 12 is pivotably fixed on the support member 13. The cover 12 is moved in directions represented with an arrow so that the upper space above the main body 11 will be opened or closed. The front portion of the cover 12 is made of a transparent synthetic resin or a semitransparent synthetic resin. Even when the cover 12 is closed as shown in FIG. 1, an internal condition thereof can be seen. The front portion of the main body 11 is provided with a display 14 of touch panel-type used for providing an indication, an input and a designation. The display unit 14 is constructed to display measurement progresses and the like. There can also be conducted such various controls, by touching the touch panel thereof, as setting a measurement condition, and providing start/stop instructions for measurements and some others.

Figure 2:
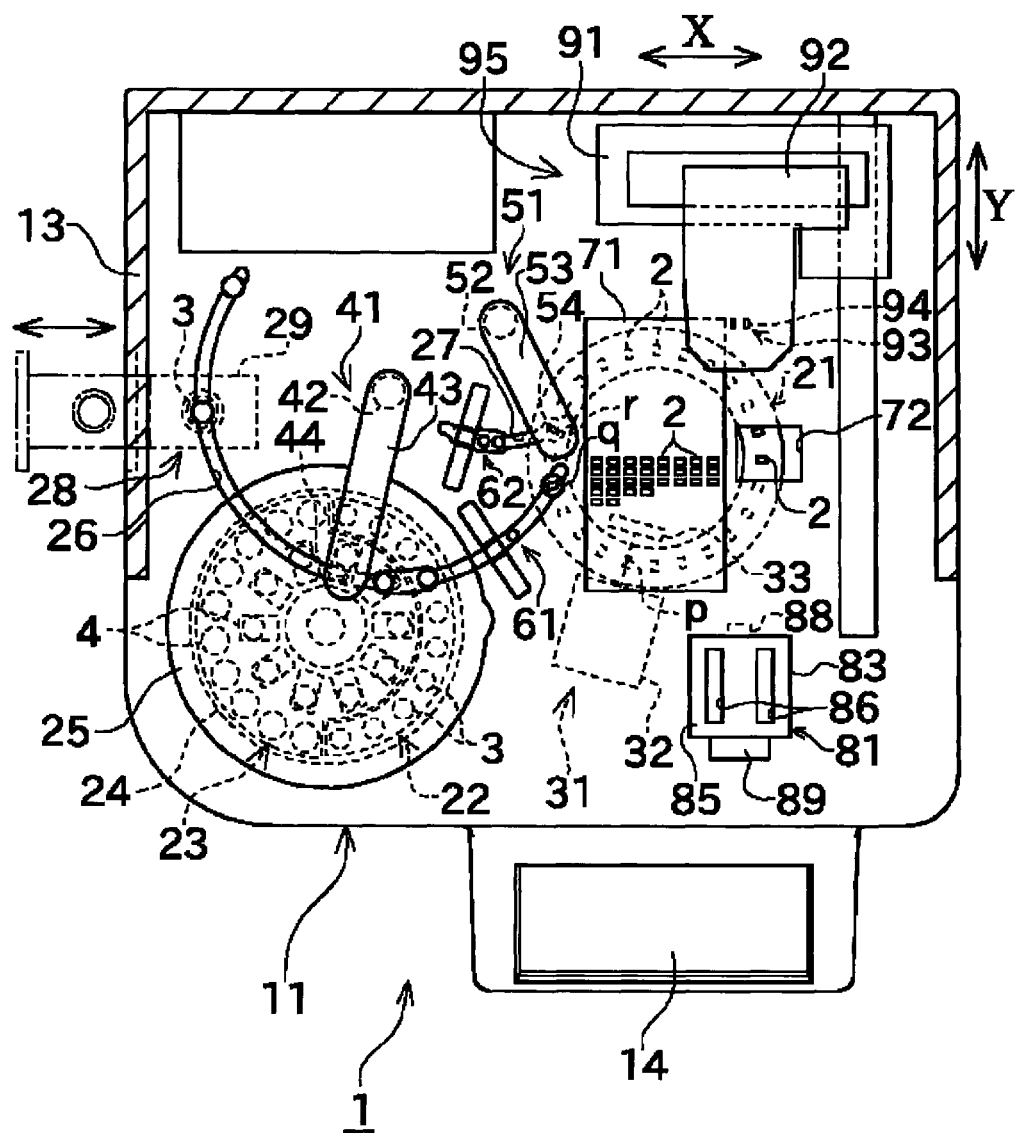
FIG. 2 is a sectional plan view of the automatic analyzer.

FIG. 2 shows a plan sectional view of the automatic analyzer 1. As shown in FIG. 2, there are provided a reaction container 21 and a specimen container holding unit 22 and a reagent vessel holding unit 23 disposed in the main body 11. The reaction container 21 is constructed in a circular form and in such a way that a plurality of cuvettes 2 are disposed on an imaginary circle in a circumferential direction at equal intervals on a horizontal surface, each functioning as a reaction vessel. The cuvette 2 is made of transparent synthetic resin and is formed as a container of a long slim shape with an opening at one end thereof. Further, the cuvette 2 is of a disposable-type, with the cuvette thrown away after its use. The reaction container 21 is rotationally driven by a predetermined pitch angle intermittently every predetermined time by a drive motor not shown. The specimen container holding unit 22 and the reagent vessel holding unit 23 are housed in a storage unit 24 shaped in a form of cylinder. The specimen container holding unit 22 is constructed to accommodate a plurality of specimen containers 3 disposed in a circumferential direction. With the reagent vessel holding unit 23, there are disposed in a circumferential direction a plurality of reagent vessels 4 each of which having a reagent therein. The storage unit 24 is rotationally driven by a motor not shown for driving the specimen container holding unit 22 and the reagent vessel holding unit 23. The drive motor turns the specimen container holding unit 22 and the reagent vessel holding unit 23 with the storage unit 24 as required so that there are supplied a plurality of specimens and desired reagents to a reagent extracting and injecting unit 41. The specimen container holding unit 22 and the upper part of the reagent vessel holding unit 23 are covered with a lid 25. Thus, a user moves the cover 12 upward and takes out the lid 25 while the apparatus is not in operation so that specimen containers 3 and reagent containers 4 can be set therein or can be exchanged with another one.

Further, the main body 11 of the automatic analyzer is provided with the second specimen storage unit holding unit 28 independently from the specimen container holding unit 22. The second specimen storage unit holding unit 28 is provided with a holder 29 which is capable of holding one specimen container 3 therein. The holder 29 is provided in the main body and slidably moved in a direction represented by an arrow in FIG. 2. The holder 29 is drawn out horizontally in a direction from the side of the main body 11 to be exposed. After a specimen container 3 is received and set thereinto, the holder 29 is pushed into the main body 11. Thus, the specimen container 3 can be set in the specimen container holding unit 28 without opening the cover 12. A light measurement unit (an absorbance measurement unit) 31 is provided in proximity of the reaction container 21. The light measurement unit 31 comprises a light source 32 and a light receiver 33. The light source 32 radiates light (for example, white Halogen light) to a cuvette 2 when the cuvette 2 in the reaction container 21 is moved in a circumferential direction and is positioned at a predetermined light measurable point "p". The light receiver 33 receives the light that passed through the cuvette 2, and measures its strength. The light source 32 comprises a plurality of filters not shown for passing therethrough light signals having specific wavelengths respectively. The filters are moved by a motor not shown so that absorbance of a light having a specific wavelength can be measured. The main body 11 is provided with an extracting and injecting unit 41 for extracting an amount of specimen in the specimen container holding unit 22 or an amount of reagent in the reagent vessel holding unit 23 and injecting a predetermined amount of the specimen or reagent into the cuvette 2 in the reaction container 21. The reagent extracting and injecting unit 41 comprises a vertical turn shaft 42, a move arm 43 fixed at the upper end of the shaft 42, and a pipette 44 held at the outermost portion of the arm and extending downwardly. The turn shaft 42 is provided with a raising and lowering mechanism and a turning mechanism not shown for raising or lowering and turning the move arm 43 and the pipette 44. An arc groove 26 is formed on the top surface of main body 11 and the top surface of the lid 25 so that the lowermost portion of the pipette 44 can be moved therein when the pipette is turned. The arc groove 26 is formed in such a way that there are interrelated a predetermined position on the reaction container 21 and in a circumferential direction thereof as an injecting point "q", the specimen container holding unit 22 and the reagent vessel holding unit 23 and the second specimen storage unit holding unit 28. The tip of pipette 44 is adapted to move in the arc groove 26. The tip of pipette 44 is inserted downwardly into the specimen container 3, reagent container 4 or the cuvette 2 by operating the raising and lowering mechanism at predetermined required positions. The pipette 44 of the reagent extracting and injecting unit 41 is coupled to an extracting and injecting mechanism not shown. Thus, the pipette 44 extracts a quantity of specimen in the specimen container 3 or an amount of reagent in the reagent container 4 and injects a quantity thereof into a cuvette 2 in the reaction container 21. A pipette washing unit 61 is disposed at a point along the arc groove 26 and exhausts unnecessary specimen and chemical reagent contained in the pipette 44 and washes the pipette 44. The main body 11 is also provided with a stirring unit 51 for stirring a reagent and a specimen injected in the cuvette 2. The stirring unit 51 comprises a vertical turn shaft 52, a move arm 53 fixed at the upper end of the shaft 52, and a stirring rod 54 held at the outermost portion of the arm and extending downwardly. The turn shaft 52 is provided with a raising and lowering mechanism and a turning mechanism not shown for raising or lowering and turning the move arm 53 and the stirring rod 54. An arc groove 27 is formed on the upper surface of the main body 11 so that the tip of the stirring rod 54 is moved in the arc groove when the move arm 53 turns. The arc groove 27 is formed in such a way that there are interrelated a predetermined position on the reaction container 21 and in a circumferential direction as a stirring point "r" and a stirring and washing unit 62 disposed in proximity of the reaction container 21. The tip of stirring rod 54 is adapted to move by means of the move mechanism in the arc groove 26. The tip of stirring rod 54 is inserted downwardly into the cuvette 2 by operating the raising and lowering mechanism at a predetermined required position. The stirring rod 54 of the stirring unit 51 is coupled to a drive motor not shown which rotates the stirring rod 54 while the rod is maintained in the cuvette 2 so that contents in the cuvette 2 is stirred up. The stirring and washing unit 62 is constructed in such a way that the stirring rod 62 with a reagent and the like stuck thereto can be washed off after a stirring operation finished. A cuvette storage unit 71 is provided on the upper surface of the main body 11. The cuvette storage unit 71 is disposed substantially above the reaction container 21 and stores a number of empty cuvettes 2 as vertically stood therein. A waste vessel container pod 81 is provided in proximity of the reaction container 21. Used cuvettes 2 are thrown into the pod 21. Further, the main body 11 is provided with a cuvette transport mechanism 95 for transporting cuvettes 2 among the reaction container 21, the cuvette storage unit 71 and the waste vessel container pod 81. The cuvette transport mechanism 95 is comprised with a first base member 91 which is slidably movable in forward and backward directions (Y-axis direction), a second base member 92 mounted on the first base member 91 and is slidably movable in right and left directions (X-axis direction), and an arm mechanism 93 coupled to the second base member 92 and is slidably movable in upward and downward directions (Z-axis direction).

Figure 3:
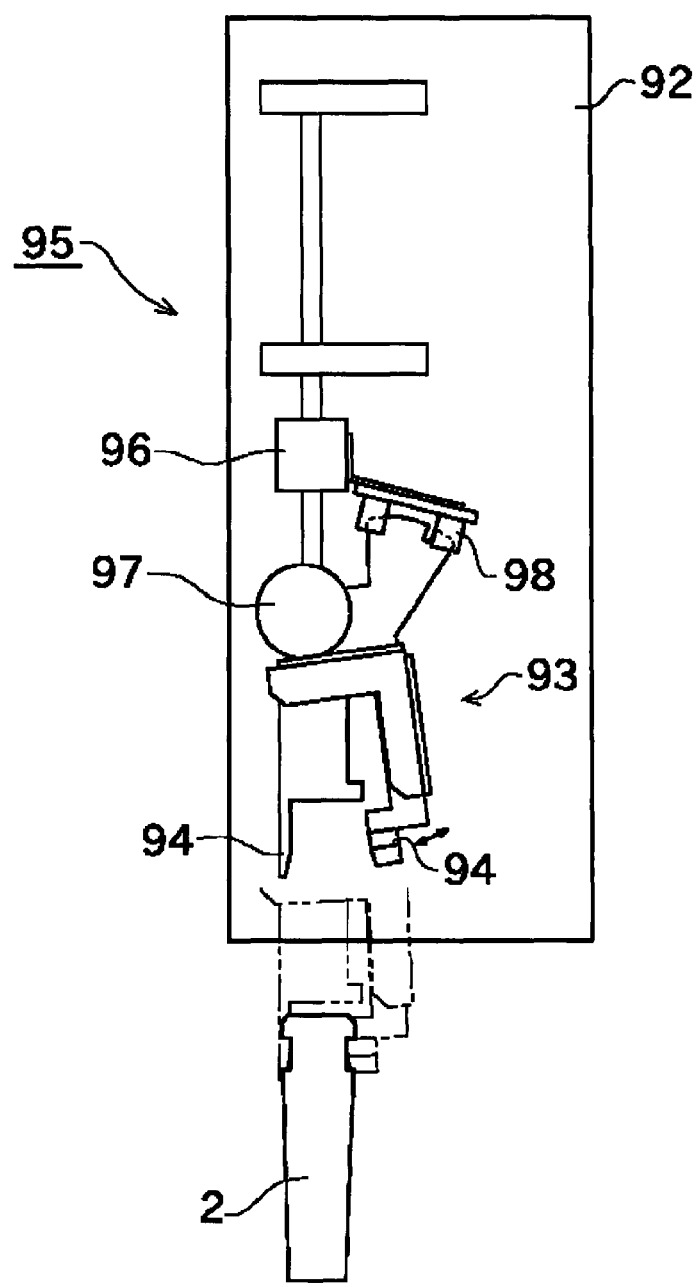
FIG. 3 is an enlarged front view of the arm part of a cuvette transport unit.

FIG. 3 illustrates a front elevation enlarged view of a main part of the arm mechanism 93. The arm mechanism 93 is fixedly attached to a slide base 96 which is slidably movable in upward and downward directions. The slide base 96 is provided with a pair of catch arms 94 and a catch motor 97 for moving one of the catch arms 94. The catch arms 94 are controlled by the catch motor 97 to open and close so that an upper portion of the cuvette 2 is gripped by the arms 94. A catch sensor 98 for detecting opening and closing of the catch arms 94 is held by the slide base 96. The catch sensor 98 functions to detect a correct catch by means of the catch arms 94 when the cuvette 2 is normally gripped by the catch arms 94. Further, the cuvette transport mechanism 95 is comprised with a drive mechanism not shown for moving the arm mechanism 93 in X-axis, Y-axis and Z-axis directions so that a cuvette 2 held by the arm mechanism 93 is transported to a desired position.

Figure 4:
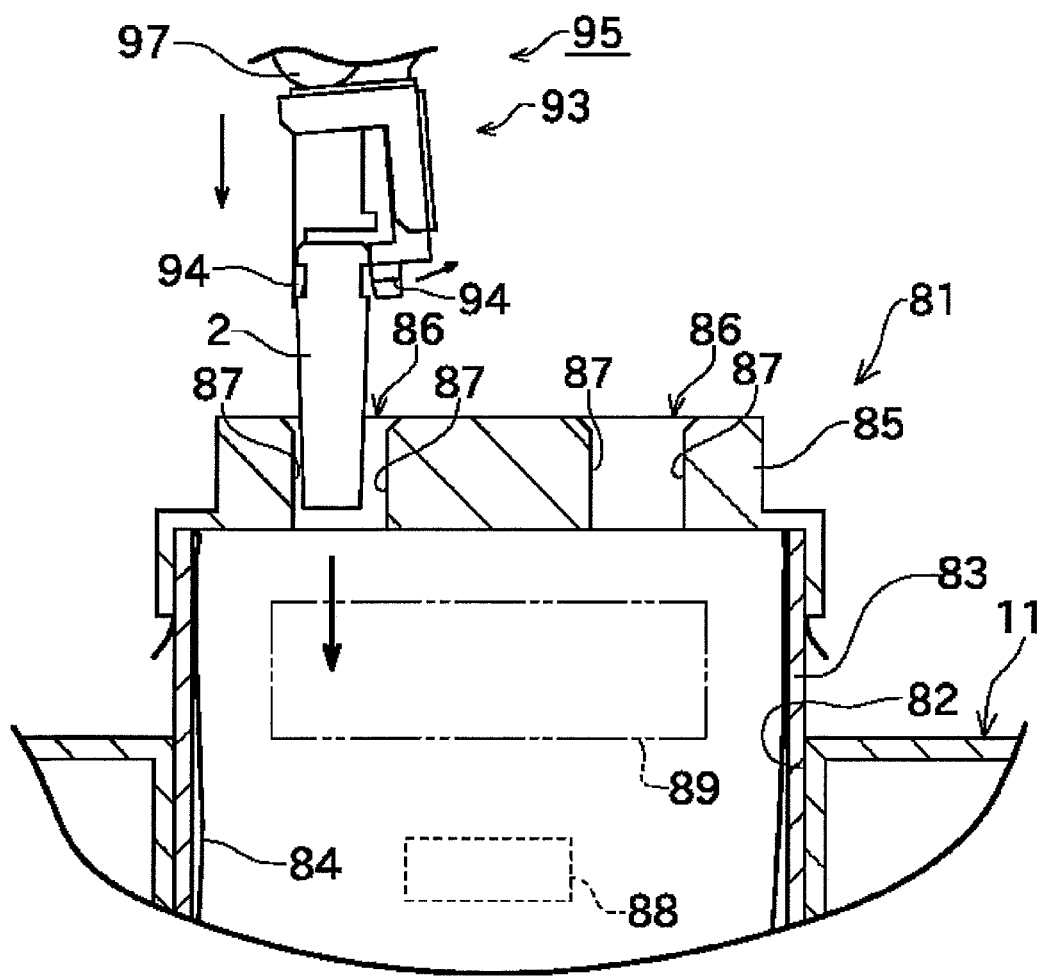
FIG. 4 is an enlarged sectional front view illustrating the construction of a dustpod and a manner of dropping a cuvette.

FIG. 4 is a front section enlarged view of the waste container pod 81 showing in detail the construction thereof. The waste container pod 81 is constructed with a concaved opening 82 formed in the upper surface of the main body 11, an attachable and detachable waste container box (storage container) 83 attached into the concaved opening 82, and a lid 85 covering the upper opening of the waste container box 83. The waste container box 83 is constructed in such a way that there are received and kept therein a predetermined quantity of used waste cuvettes 2. A bag 84 made of plastic or paper is inserted into and kept in the waste container box 83. A bore 86 is formed in the lid 85 to drop a cuvette 2 therethrough into the box 83. With the embodiment of the invention, there are formed two vertical straight bores 86 disposed in parallel with each other.

The bore 86 has an extensive slit part the width of which is determined to be slightly wider than that of the cuvette 2. Inner guide walls 87 of each of the bores 86 are formed vertically. The two guide walls are in parallel with each other and face each other. A demount sensing sensor 88 is installed in proximity of the upper end of the concaved opening 82. The demount sensing sensor 88 detects a removal of the waste container box 83 when the box 83 is pulled up from the concaved opening 82. The waste container box 83 is held in such a way that an upper portion of the box 83 is protruded with respect to the upper surface of the main body 11 having the concaved opening 82. The protruded portion of the box 83 is provided with a handle 89 which makes the waste container box 83 easier to be carried and also enables the box 83 easily to be mounted or demounted.

As shown in FIG. 2, a window 72 is formed on the upper surface of the main body 11 in proximity of the cuvette storage unit 71. The window 72 is located above the reaction container 21. A part of the reaction container 21 can be seen through the window 72. Thus, the cuvette transport mechanism 95, when driven, catches and carries an empty cuvette 2 in the cuvette storage unit 71, and places the cuvette 2 at a required position in the reaction container 21 from the window 72. The cuvette transport mechanism 95 catches a used cuvette 2 set in the reaction container 21, and takes out the used cuvette 2 through the window 72. Then, as shown in FIG. 4, the cuvette transport mechanism 95 drops the used cuvette 2 through the bore 86 into the waste container pod 81 to be disposed of.

Figure 5:
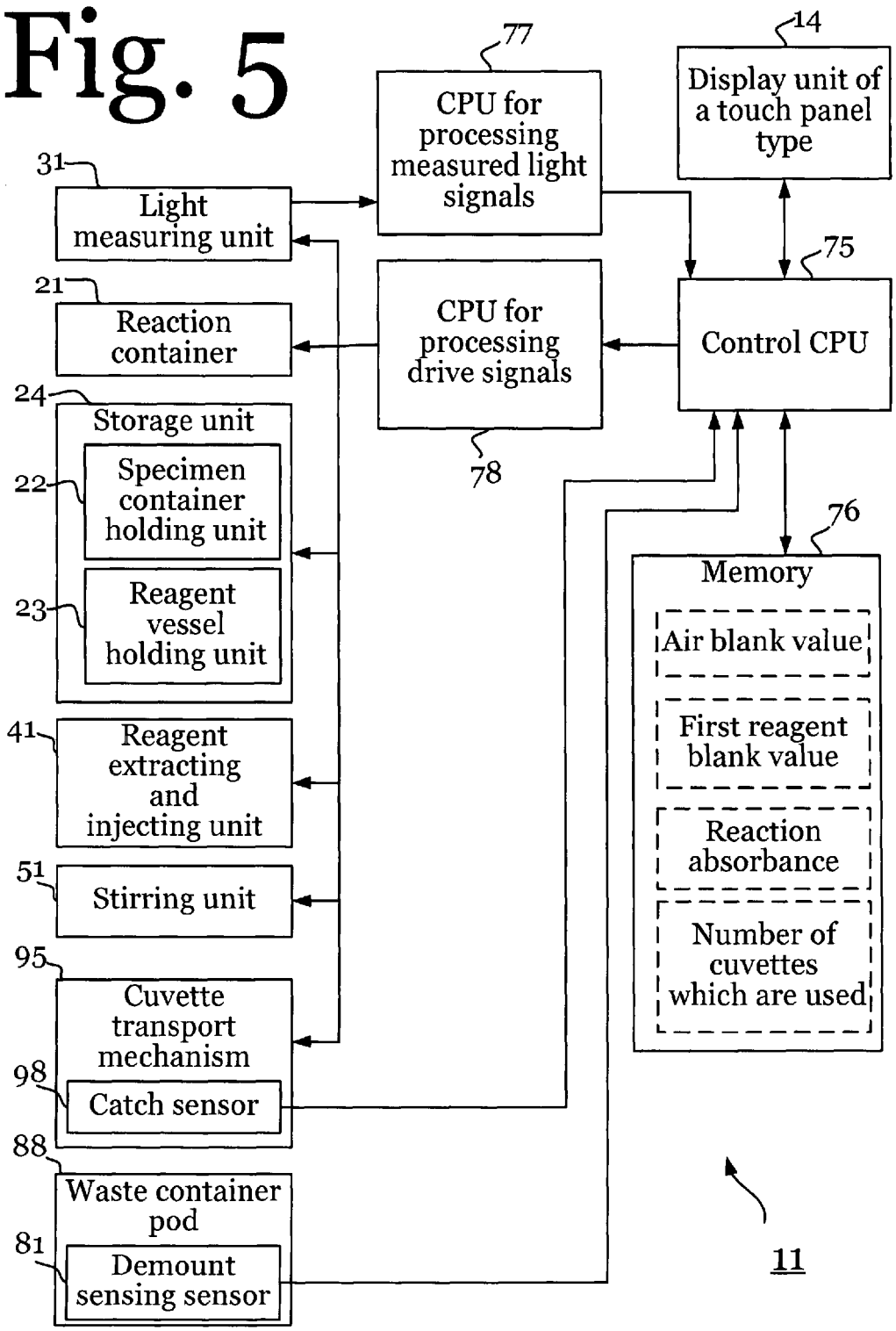
FIG. 5 is a block diagram of an automatic analyzer according to the invention.

Referring to a block diagram shown in FIG. 5, an electric arrangement of an analyzer according to the invention will be explained. As shown in FIG. 5, the apparatus 11 comprises a control CPU 75 as an arithmetic logical unit and a memory 76 to store various kinds of information. Further, the apparatus 11 is comprised with a CPU 77 for processing measured light signals and with a CPU 78 for processing drive signals. The CPU 77 for processing measured light signals performs arithmetic operations on signals obtained by the light measuring unit 31, and supplies a signal representative of an absorbance to the control CPU 75. The CPU 78 for processing drive signals transmits drive signals in response to instruction signals from the control CPU 75 to the light measuring unit 31, the reaction container 21, the storage unit 24, the reagent extracting and injecting unit 41, the stirring unit 51 and the cuvette transport mechanism 95 to operate the units as required respectively. It is to be noted that with the embodiment according to the invention, the control CPU 75 and the CPU 78 for processing drive signals correspond to the control unit. There are supplied to the control CPU 75 signals from the catch sensor 98 included in the cuvette transport mechanism 95 and signals from the demount sensing sensor 88 provided for the waste container pod 81. The control CPU 75 is coupled to the display unit of a touch panel type 14 so that various kinds of input and output signals representative of measurement conditions, measurement results obtained and the like. The memory 76 is arranged to store measurement results obtained, such as an air blank value (first blank value), the first reagent blank value (second blank value), a reaction absorbance, and the like. Further, the memory 76 is arranged to store the number of cuvettes 2 which are used for measurements and dropped into the waste container pod 81 and also measurement conditions frequently used by users.

Figure 6:
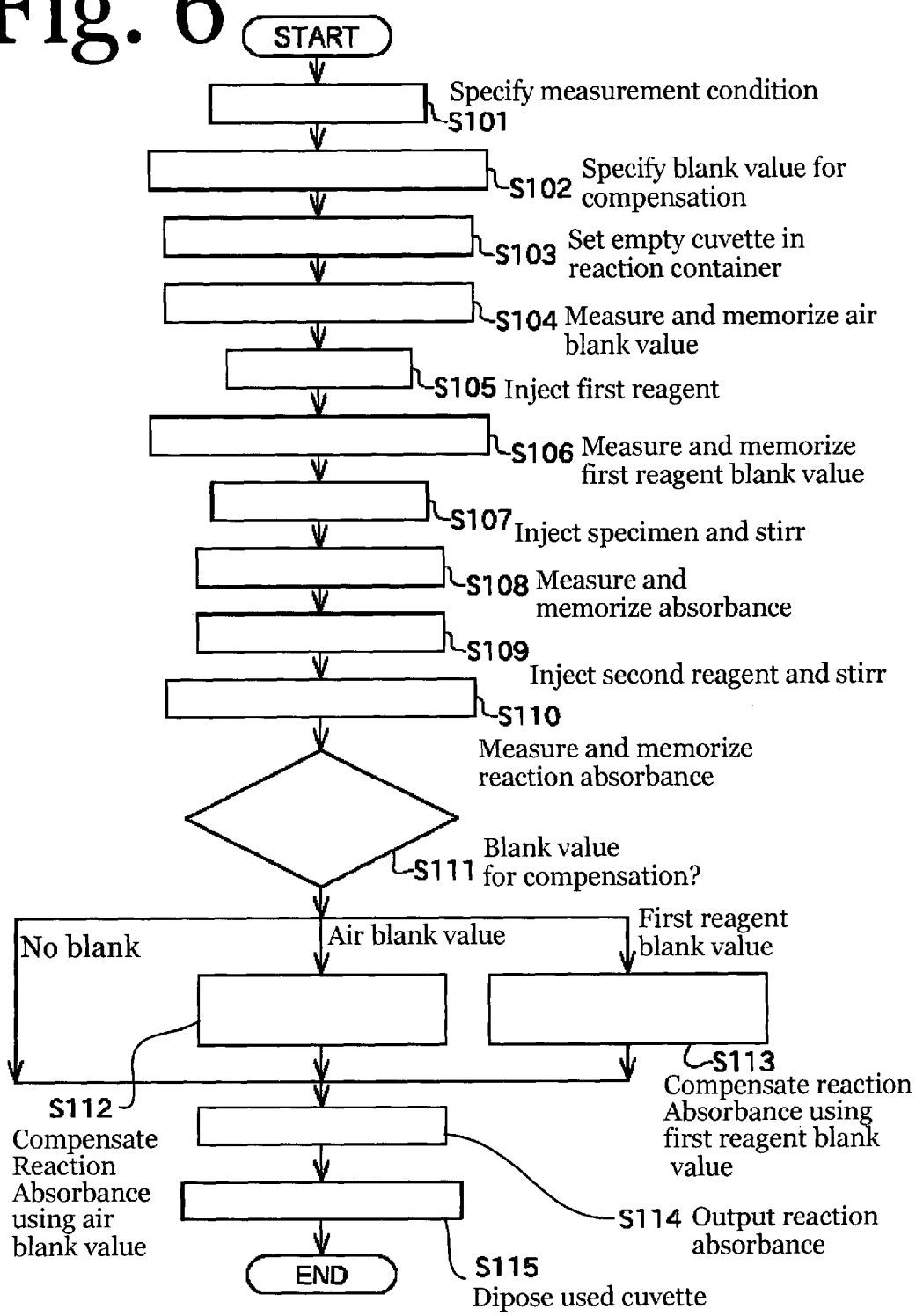
FIG. 6 is a flow chart illustrating the operation of an automatic analyzer.

There will be explained hereinafter an operational flow of an measurement performed by the automatic analyzer according to an embodiment of the invention and constructed having been explained in the foregoing, by referring to a flow chart shown in FIG. 6. At first, before starting a measurement, specimen containers 3 and reagent vessels 4 are set in the specimen container holding unit 22 and the reagent vessel holding unit 23 respectively. Then, an operation screen of the display unit 14 is touched by a finger of a user to provide inputs so that a measurement condition is specified (S101). As a measurement condition, for instance, there are provided quantities of a specimen and a reagent injected into a cuvette 2, reaction time, a photometry wave length, a method of measuring absorbance and the like. Next, a blank value to be used for a compensation in calculating reaction absorbance is predeterminedly specified (S102).

With the automatic analyzer 1 of the embodiment according to the invention, there is used either of a blank value (air blank value) obtained with an empty cuvette 2 set in the reaction container 21 or a blank value obtained with a cuvette 2 with a reagent injected thereinto (first reagent blank value as the second blank value), which is different from a blank value obtained with pure water and normally used, to compensate reaction absorbance which will be explained hereinafter.

With an apparatus according to an embodiment of the invention, there is determined a way to correct an absorbance based on which one of the blank values (or not to make a correction thereon) which will be explained hereinafter.

Figure 7:
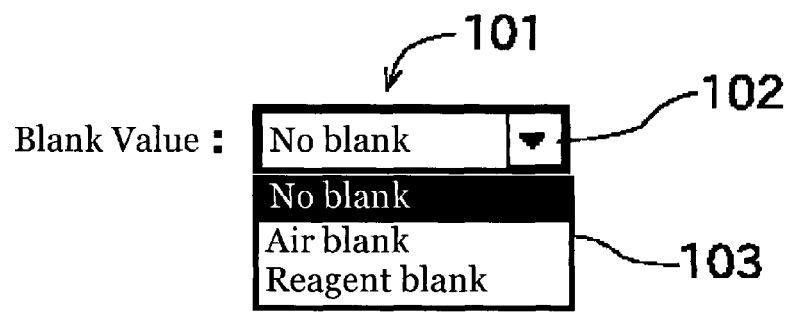
FIG. 7 is a display example on the screen of the display unit when a blank value is specified.

Thus, an operation screen as shown in FIG. 7 will be displayed on the display unit 14 at a time instant when a measurement condition is determined or afterwards. With the operation screen, on the right side of a label "Blank:" representing a blank value, there is displayed a pull-down list 101. When a button 102 having a triangle mark pointing downward thereon is touched by a finger, there will be displayed a list of blanks 103 for specifying a blank value. In the list 103 appeared, there are displayed "No Blank", "Air Blank", and "Reagent Blank". "No Blank" means that an absorbance is not compensated. "Air Blank" means that an absorbance is compensated with an air blank value. "Reagent Blank" means that an absorbance is compensated with a first reagent blank value. When one of the three kinds of blank indications is touched, the touched and selected blank is displayed in the pull-down list 101, and the list 103 will disappear. In this way, there is specified one of the "No Compensation", "Compensation with Air Blank Value" and "Compensation with First Reagent Blank Value". The selection of compensation can be made for a specimen and a measurement parameter, and resultant specified contents will be stored in the memory 76. When a measurement is started, at first, the cuvette transport mechanism 95 takes out an empty cuvette 2 from the cuvette storage unit 71 and sets it in the reaction container 21 (S103). It is to be noted that there can be specified by means of the display unit 14 of touch-panel type a way to select one of a number of cuvettes 2 stored in the cuvette storage unit 71. It is also possible to automatically select desired cuvettes successively in an order having been predetermined. As the reaction container 21 is rotated sequentially, a cuvette 2 set in the reaction container 21 reaches a light measurement position "p" after a time later, and an absorbance is measured by the photometry unit 31 (S104).

Since the cuvette 2 is empty, a measurement value obtained by the photometry unit 31 will be an absorbance for the air in a cuvette 2 and for the cuvette 2 (an air blank value and a cuvette blank value respectively). A measured air blank value is memorized in memory the 76 in the main body 11. After the measurement of an air blank value, the reaction container 21 continues to rotate sequentially. When the cuvette 2 moves to an extracting and injecting position "q", the reagent extracting and injecting unit 41 is driven to extract a first reagent from the reagent vessel 4 in the reagent vessel holding unit 23, and injects a quantity of the reagent into the cuvette 2 (S105). Thus, only the first reagent is contained in the cuvette 2. As the reaction container 21 further rotates, the cuvette 2 makes a complete rotation in a circle to come again to the light measuring position "p". Then, a light measurement will be conducted by the photometry unit 31 (S106). As only the first reagent is contained in the cuvette 2 at this moment, a measured value obtained by the photometry unit 31 is an absorbance of the first reagent in the cuvette 2 (first reagent blank value). The first reagent blank value is memorized in the memory 76 provided in the main body 11. After the measurement of the first reagent blank value, the cuvette 2 in the reaction container 21 reaches the extracting and injecting position "q" again. The reagent extracting and injecting unit 41 absorbs a quantity of specimen from the specimen container 3 in the specimen container holding unit 22, and discharges a predetermined quantity of the specimen into the cuvette 2. When the cuvette 2 in the reaction container 21 is further rotated to reach the stirring position "r", the stirring rod 54 is inserted into the cuvette 2 and rotated by the stirring unit 51 to stir the first reagent and the specimen therein (S107). After the stirring operation performed, the reaction container 21 is turned so that the cuvette 2 will be moved. After making a plurality of rotations, when the cuvette 2 is brought to the light measuring position "p", a light measurement is made by the light measuring unit 31. A measurement value obtained thereby is stored in the memory 76 (S108). Then, the cuvette 2 reaches the extracting and injecting position "q" where the extracting and injecting unit 41 extracts second reagent from the reagent vessel 4 in the reagent vessel holding unit 23 and injects a quantity thereof into the cuvette 2. When the cuvette 2 is further moved to the stirring position "r", the stirring rod 51 stirs substances in the cuvette 2 in the same way as above explained. Thus, the first reagent, the specimen and the second reagent are stirred up in a good manner to react with each other (Slog). When the cuvette 2 is moved to the light measuring position "p", a light measurement is made by the photometry unit 31 (S110). In this way, an absorbance after reactions can be obtained. It is to be noted that an absorbance may be measured only once after the cuvette 2 makes a plurality of rotations in a circle, or an absorbance may be measured every rotation of the cuvette 2, i.e., every time the cuvette 2 passes the light measuring position "p" after required reactions made. Measured absorbances are stored by the memory provided in the main body 11.

Next, there is read out from the memory 76 and examined a blank value designated at a step S102, i.e., the content specified on the screen shown in FIG. 7 (S111). If a requirement to compensate with an air blank value is designated, an operation is advanced to a step S112 where a compensation is made by subtracting an air blank value measured at a step S104 from the absorbance measured at a step S110. If a requirement to compensate with a first reagent blank value is designated, an operation is advanced to a step S113 where a compensation is made by subtracting a first reagent blank value measured at a step S106 from the absorbance measured at a step S110.

If no compensation (No Blank) is designated, neither one of a step S112 nor a step S113 is performed. With the automatic analyzer which is compact and of cuvette disposable type, by conducting an operation in the way explained in the foregoing, i.e., an absorbance is compensated based on an air blank value or on a first reagent blank value, it will be possible to measure absorbance (ingredient analysis value) with small variation and with high precision. It is to be noted that in measuring absorbance, generally, pure water is poured into a cuvette and an absorbance (a water blank value) is measured, and the water blank value is subtracted from an absorbance for reacted liquids so that the reaction absorbance is compensated. However, with the method using a water blank value for compensation, there will be required a step for pouring pure water into a cuvette and a step for draining the pure water therefrom so that the measurement efficiency will be lowered. An amount increase of pure water used will increase running cost and also require a special mechanism to drain pure water from a cuvette. Thus, it will be necessary to reduce the size and weight of an automatic analyzer. But, the method according to the invention for compensating absorbance based on an air blank value or a first reagent blank value does not need pure water and makes advantageously the construction of an automatic analyzer simpler. Further, as the embodiment according to the invention is capable of choosing an air blank value or a first reagent blank value for a compensation depending on relevant conditions, an appropriate selection of compensation methods will further improve measurement precision of absorbance. For example, if absorbance is too high depending on a kind of reagent, a first reagent blank value is not used as a blank value. Thus, an air blank should be used instead. Further, it is also possible to select "No Blank" for not compensating an absorbance. Thus, it will be possible to flexibly obtain an absorbance depending on various conditions. Reaction absorbance compensated depending on relevant conditions is output to the display unit (S114). When a cuvette 2 having liquids reacted therein is further moved to reach the window 72, the transport mechanism 95 takes a cuvette 2 from the reaction container 21 and dispose it into the waste container pod 81 (S115).

As explained above, a series of measurements and operations are finished. It is to be noted that although a series of operations for one cuvette 2 has been explained to be conducted in accordance with a flowchart shown in FIG. 6, a plurality of specimens are examined using a certain number of reagents in practice. Thus, a plurality of cuvettes 2 are set at the same time in the reaction container 21, and measurement operations are performed in accordance with the flowchart in parallel simultaneously and respectively. It is to be noted that the inventors of the present application have made experiments to measure absorbance using twenty-four cuvettes having specimen and reagent injected thereinto for each of (a) No compensation, (b) Compensation using an air blank value and (c) Compensation using first reagent blank value. The result of the experiment reveals that standard deviation of absorbance for (a) No compensation is 4.9, standard deviation of absorbance for (b) Compensation using an air blank value is 2.3, and standard deviation of absorbance for (c) Compensation using first reagent blank value is 1.8. As explained in the foregoing, it has been found that variation of compensated absorbance obtained by using an air blank value or first reagent blank value is better suppressed with respect to the one obtained with the No compensation.

Next, there will be explained hereinafter the way disposing of cuvettes 2 to the waste container pod 81. The cuvette transport mechanism 95 used for disposing of used waste cuvettes 2 is comprised with the catch arms 94 capable of gripping the upper part of a cuvette 2, as shown in FIG. 3. As shown in FIG. 4, the bores 86 are formed in the waste container pod 81 and are provided with guide walls 87. When a used cuvette 2 is disposed of, the cuvette transport mechanism 95 is controlled by the control CPU 75 and the CPU 78 for processing drive signals in such a way that the upper portion of a cuvette 2 is first gripped by the catch arms 94 and then the lower portion of the cuvette 2 is inserted in the bore 86, as shown in FIG. 4. The cuvette transport mechanism 95 drives the catch motor 97 to release from the catch arms 94 a cuvette 2 which is in proximity of the guide walls 87 or in contact therewith. It is to be noted that FIG. 4 shows a state at a time instant when a cuvette is released from the catch. Thus, the cuvette 2 falls down along the guide wall 87 at a moment when it is released from the catch. As the cuvette 2 is guided by the guide wall 87 and thus the attitude thereof is stabilized so that it will be possible to prevent reagent and specimen in the cuvette 2 from being spilled around the waste container pod 81 and to prevent the surrounding area from being polluted.

With automatic analyzers such as the present embodiment, due to a quantity of reagent unintentionally attached to and static electricity generated on a cuvette 2, the cuvette 2 will adhere to the catch arms 94 so that it will be harder for the cuvette 2 to drop straight down. With an automatic analyzer according to the invention, disposal operations can be conducted smoothly, since cuvettes 2 can be fallen straight down to be disposed of. While the catch arms 94 is moved toward the lowest position, it is driven by the catch motor 97 to release a cuvette 2 from the catch arms 94 as represented with an arrow in FIG. 4. Thus, since a cuvette 2 gains momentum in a downward direction and is released from the catch arms 94, it will be possible to prevent errors in dropping cuvettes downward from being made. Thus, it can perform a disposal operation smoothly. The bore 86 is formed in a form of slit as shown in FIG. 2. The width of the slit is determined in such a way that a cuvette 2 is inserted thereinto. Thus, it is easy for the side of the guide wall 87 to be in proximity of or in contact with the guide wall 87, which enables a cuvette 2 to drop straight down still more easily. Since the bore 86 is shaped in a form of slit, a sufficient opening area of the slit is secured and it will be possible to prevent a used cuvette 2 from being clogged. The cuvette transport mechanism 95 is constructed to drop a used cuvette down at a different position along a longer side of the rectangular opening of the bore 86. Thus, a cuvette 2 is dropped at a position along the side of the slit which is different from the previous position so that cuvettes 2 are not accumulated in a convex form, but are uniformly accumulated in the waste container box 83. The disposal method prevents the waste container box 83 from becoming full in a short time. Trouble of maintenance therefor can be reduced. Further, with the embodiment according to the invention, there are formed two bores 86. The cuvette transport mechanism 95 is constructed to drop waste cuvettes 2 from each of the different bores 86. Thus, as it is controlled to drop a cuvette 2 through a bore 86 which is different from the one used previously, in the same way as in the foregoing, cuvettes 2 are not accumulated in a convex form, but are accumulated uniformly in the waste container box 83 so that it will prevent the box 83 from becoming full in a short time. With the embodiment according to the invention, a first cuvette 2 is dropped at one side of the one bore 86, a second cuvette 2 is dropped at the other side of the same bore 86, a third cuvette 2 is dropped at one side of the other bore, and a fourth cuvette 2 is dropped at the other side of the same other bore 86. In this way, drop positions of waste cuvettes are changed in a rotational manner. The way of throwing cuvettes away thereinto enabling cuvettes to be accumulated uniformly. With the embodiment according to the invention, the memory 76 of the main body 11 stores the number of the cuvettes thrown into the waste container pod 81. The control CPU 75 increases its count by one every time a cuvette 2 is disposed of. If the count representative of the number of cuvettes disposed of reaches a predetermined number, an alarm is displayed in the display unit 14 to notify a user thereof. The predetermined number is the number of cuvettes making waste container box 83 substantially full. This arrangement will inform a user of a state that the waste container pod 81 has become substantially full precisely. As compared to, for instance, a way to detect quantity of cuvette sedimentation in the waste container box 83 with a sensor directly, the way explained in the foregoing has advantages as performing detections without errors and constructing the apparatus at a reasonable cost. When it is detected by the removal detection sensor 88 that the waste container box 83 is pulled out from the concaved opening 82, the control CPU 75 resets the memory 76 so that the number of waste cuvettes having been stored is set to zero. As the number of waste cuvettes is automatically reset to zero when it is detected that the waste container box 83 is pulled out from the concaved opening 82, there is not required a special reset operation and thus, a user's work amount will be reduced. The waste container box 83 shown, for instance, in FIG. 2 is provided with a handle 89 for taking it from the main body 11. Further, it is possible to put a bag 84 disposed in the waste container box 83. Thus, the waste container box 83 can be easily removed from the main body 11 with a help of the handle 89 attached thereto.

Since cuvettes 2 are successively thrown into and accumulated in the waste container box 83, the bag 84 containing the cuvettes 2 are disposed of.

Thus, it will be easy to handle used cuvettes. It will also be possible to prevent reagent and others from being adhered to a hand of a user. Further, the main body 11 is comprised with the second specimen storage unit holding unit 28 having the holder 29 slidably moved. The holder 29 is first drawn horizontally out of the main body 11 and accepts a specimen container 3 to be set therein and then is pushed into the main body 11 so that a quantity of specimen extracted from the second specimen storage unit holding unit 28 is injected into a cuvette 2 by means of the reagent extracting and injecting unit 41. When an extraordinary or urgent measurement becomes necessary while a normal analyzing measurement is being conducted, this construction enables the cover 12 to be opened and a special unexpected measurement to be performed uninterruptedly without stopping the operation of the apparatus by merely setting the specimen container 3 in the second specimen storage unit holding unit 28. Thus, a flexible measurement scheduling becomes possible and a high efficiency of measurement can be well maintained. It is to be noted that when the specimen in an urgent case is set in the second specimen storage unit holding unit 28, the display unit 14 of touch-panel type is operated by a user to stop the reagent extracting and injecting unit 41 and to set a specimen container 3 in the holder 29. Accordingly, the arrangement will prevent the reagent extracting and injecting unit 41 from being damaged. It is to be noted that there is stopped only the reagent extracting and injecting unit 41 to operate. The cuvette transport mechanism 95 and other units continue operations without interruption. Thus, a large degradation of measurement efficiency will not occur. After a specimen container 3 is set in the second specimen storage unit holding unit 28, the display unit 14 is operated again so that the operation of reagent extracting and injecting unit 41 is reopened.

Next, there will be explained hereinafter an arrangement to detect a mounting or a demounting of a cuvette 2 in the reaction container 21.

Since the number of cuvettes 2 which are set in the reaction container 21 is limited, cuvettes having been set in the reaction container 21 have to be replaced with new cuvettes after absorbance of the respective cuvettes are measured, when many specimens and many kinds of reagents are injected thereinto and used to measure absorbance thereof.

Figure 8:
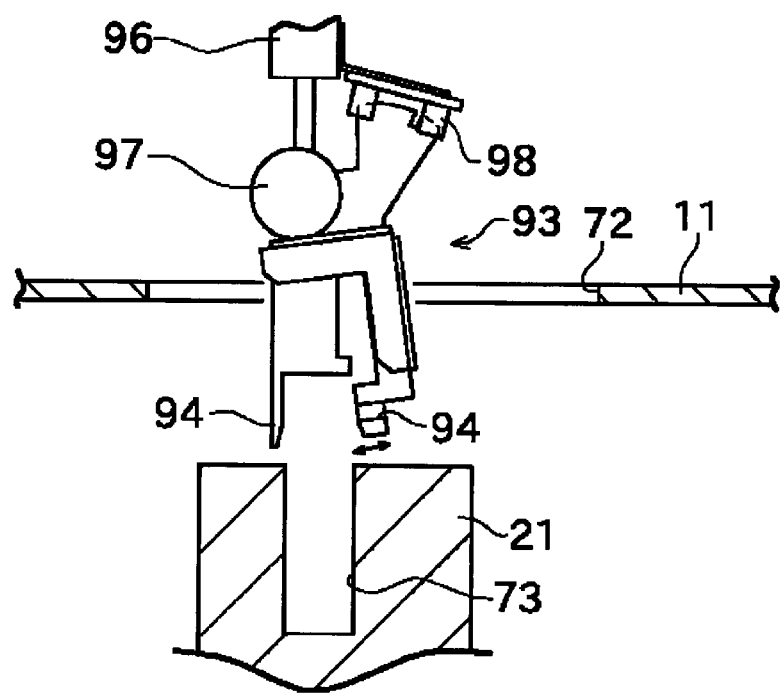
FIG. 8 is a view of a part of the cuvette transport unit illustrating a manner for determining whether a cuvette has been set in the reaction vessel container.

However, there may be cases that a cuvette 2 is left in the reaction container 21 due to such an error that the cuvette transport mechanism 95 fails to take out the cuvette. If a new cuvette 2 is moved to be set at a position where the above cuvette has been left in the turntable, the cuvettes will collide with each other so that the cuvettes and the apparatus will be damaged. In order to solve the above problem, the control CPU 75 and the CPU 78 for drive signal processing control the cuvette transport mechanism 95, as will be explained hereinafter in a stage before a new cuvette 2 is set in the reaction container 21 (corresponding to a step S103 in FIG. 6). As shown in FIG. 8, the arm mechanism 93 without holding a cuvette 2 is lowered through the window to the position directly above the reaction container 21, i.e., directly above a position where a cuvette 2 is supposed to be set. The catch motor 97 is driven at a position directly above a hole 73 in a concave shape formed for mounting or demounting a cuvette 2 in the reaction container 21 to have a catch operation performed by the catch arms 94. If a cuvette 2 is left in the reaction container 21 due to some causes as cuvette demount errors, the cuvette 2 will be caught by the catch arms 94, which is detected by the catch sensor 98. The control CPU 75 controls the display unit 14 to indicate an error message that another cuvette 2 is left and occupied at the position where a new cuvette 2 is supposed to be set in. If the catch sensor 98 does not detect a catch of a cuvette 2, it is determined that a cuvette is not found at the position another cuvette is supposed to be set in. Thus, the cuvette transport mechanism 95 first moves the catch arms 94 to the cuvette storage unit 71 to grip an empty cuvette 2, and lowers the catch arms 94 through the window 72 to set a cuvette into an expected position. Then, a measurement will be made. As explained above, there is provided an arrangement to detect whether a cuvette is set or not in the reaction container 21. Assuming that sensors for detecting a mount or a demount of a cuvette are disposed in the set holes 73 respectively, the arrangement will be costly and complicated in construction. With the embodiment according to the invention, a mount or demount of a cuvette 2 is detected by only the catch sensor 98 included in the cuvette transport mechanism 95. It is to be noted that the operation for detecting a mount or demount of a cuvette is performed while a cuvette transferring operation is not being conducted, i.e., the cuvette transport mechanism 95 is idling. With this arrangement, there will be detected a mount or demount of a cuvette 2 by, at the same time, maintaining its measurement efficiency well. Further, as explained above, if an old cuvette 2 is left at a position where a new cuvette is supposed to be set, the control CPU 75 controls to display the error message, and also the cuvette transport mechanism 95 forcibly removes the old cuvette 2 from the set hole 73 and throws it away into waste container pod 81. With the arrangement, an empty cuvette 2 for a new measurement can be set in the reaction container 21 so that measurements can be made continuously.

Although there have been explained heretofore preferred embodiments according to the invention, the constructions hereof can be modified, for instance, as in the following. Although an air blank value or a first reagent blank value is chosen manually by a user, it is also possible for the control CPU 75 to automatically select an air blank value or a first reagent blank value based on measurement conditions and a first reagent blank value measured to compensate absorbance measured. Determining a blank value for a compensation as shown in FIG. 7 is not necessarily be made before a measurement is started. The determination can be made after absorbance is measured. When an air blank value was determined in S102 of FIG. 6, it can be constructed not to measure the first reagent blank value of S106. It is to be noted that if a first reagent blank value is determined at a step S102, it may be constructed not to measure an air blank value at a step S104. It is to be noted that although the determination of a blank value for a compensation is made by using a pull-down box as shown in FIG. 7, it is also possible to use a check box or a radio button or the like for determination. It is to be noted that although the display unit 14 of touch-panel type is used as having been explained in the foregoing, it is also possible to use an external input means such as a key board which is connected to a connection terminal of the main body 11 and selects one of the blank values for a compensation. It is also possible to use a switch of button-type provided in the main body 11 to select one of the blank values. It is to be noted that although the control CPU 75, the measured light signal process CPU 77 and the drive signal process CPU 78 are used to perform assigned jobs, it is also possible to use one CPU to perform the jobs. It is to be noted that although the one extracting and injecting unit 41 is used both for specimen and reagent with the embodiment according to the invention, it is also possible to have an extracting and injecting unit for specimen and another extracting and injecting unit for reagent separately. It is to be noted that although, with the embodiment according to the invention, the specimen container holding unit 22 and the reagent vessel holding unit 23 are housed in the same storage unit 24, the specimen container holding unit 22 and the reagent vessel holding unit 23 can be provided separately. It is to be noted that it is also possible to appropriately change the construction of the waste container pod 81, the shape of the waste container box 83, and the shape or the number of the bore 86 when necessary. With the foregoing embodiment, there is used the bore 86 shaped in a rectangle with two of the four sides being straight and long. It is also possible to use, for instance, a long and curved rectangle or a bore in a form of H character. With the embodiment according to the invention, first reagent and second reagent are used for a measurement. It is also possible to use only first reagent without using second reagent depending on kinds of reagents and kinds of measurements, which do not depart from the spirit of the present invention and is within the scope of the invention.

What is claimed is:

1. An automatic analyzer comprising:
    a reaction container for having a plurality of disposable reaction vessels set therein;
    a reagent injecting unit for injecting a reagent into the disposable reaction vessel;
    a specimen injecting unit for injecting a specimen into the disposable reaction vessel;
    an absorbance measuring unit for emitting light to the disposable reaction vessel and measuring reaction absorbance of the disposable reaction vessel having a reagent and a specimen injected therein and reacted with each other, and also measures a first blank value representing absorbance of the disposable reaction vessel which is empty and a second blank value representing absorbance of the reaction vessel having only a reagent injected thereinto, wherein the absorbance measuring unit is provided with a designation unit to designate one of the first blank value and the second blank value to be used as a blank value;
    a controller for controlling the absorbance measuring unit;
    an arithmetic unit for calculating based on outputs of the absorbance measuring unit compensating the disposable reaction absorbance based on the blank value selected in the designation unit;
    a waste vessel storage unit for storing waste disposable reaction vessels;
    a transport unit for removing from the reaction container the disposable reaction vessel after measuring and dropping the disposable reaction vessel into the waste vessel storage unit; and
    a control unit for controlling the transport unit.

2. The automatic analyzer as claimed in claim 1 wherein the absorbance measuring unit is operable to measure both the first blank value and the second blank value.

3. The automatic analyzer as claimed in claim 1 wherein the absorbance measuring unit is adapted to measure both the first blank value and the second blank value and is provided with a designation unit to select one of the first blank value and the second blank value to be used as a blank value in compensation for the reaction absorbance in the arithmetic unit or to be capable of making a designation so that the arithmetic unit does not compensate the reaction absorbance.

4. The automatic analyzer as claimed in claim 1, further comprising:
    a memory unit for memorizing the number of the waste disposable reaction vessels thrown away by the transport unit;
    wherein the waste vessel storage unit has a storage container mountable in and demountable from the main body and a demount sensor for detecting that the storage container is removed from the main body of the analyzer, and the control unit increases its count by one each time a used waste disposable reaction vessel is thrown away into the waste vessel storage unit and memorizes a resultant count in the memory unit and provides a user with an alarm at a time instant when the count reaches a predetermined count value and resets the memory content in the memory unit when the demount sensor detects that the storage container is removed from the main body.

5. The automatic analyzer as claimed in claim 1, further comprising:
    a specimen storage unit;
    second specimen storage unit for storing specimens;
    wherein the second specimen storage unit provides a holder which is slidably movable, with the holder receiving the specimen container set therein when the holder is drawn out of the main body and being pushed into and set in the main body so that a specimen can be injected by the specimen injecting unit and thus a measurement for a specimen in the second specimen storage unit can be made in addition to measurements for specimens in the specimen storage unit.

6. An automatic analyzer comprising:
    a reaction container for having a plurality of disposable reaction vessels set therein;
    a reagent injecting unit for injecting a reagent into the disposable reaction vessel;
    a specimen injecting unit for injecting a specimen into the disposable reaction vessel;
    an absorbance measuring unit for emitting light to the disposable reaction vessel and measuring reaction absorbance of the disposable reaction vessel having a reagent and a specimen injected therein and reacted with each other, and also measures at least one of a first blank value representing absorbance of the disposable reaction vessel which is empty and a second blank value representing absorbance of the reaction vessel having only a reagent injected thereinto;
    an arithmetic unit for calculating based on outputs of the absorbance measuring unit compensating the disposable reaction absorbance based on at least one of the first blank value and the second blank value;
    a waste vessel storage unit for storing used waste disposable reaction vessels;
    a transport unit for removing from the reaction container a disposable reaction vessel after reaction absorbance thereof is measured and dropping the disposable reaction vessel into the waste vessel storage unit;
    a control unit for controlling the transport unit;
    a memory unit for memorizing the number of the waste disposable reaction vessels thrown away by the transport unit;
    wherein the waste vessel storage unit has a storage container mountable in and demountable from the main body and a demount sensor for detecting that the storage container is removed from the main body of the analyzer, and the control unit increases its count by one each time a used waste disposable reaction vessel is thrown away into the waste vessel storage unit and memorizes a resultant count in the memory unit and provides a user with an alarm at a time instant when the count reaches a predetermined count value and resets the memory content in the memory unit when the demount sensor detects that the storage container is removed from the main body.

7. The automatic analyzer as claimed in claim 1 further comprising:
a specimen storage unit;
second specimen storage unit for storing specimens;
wherein the second specimen storage unit provides with a holder which is slidably movable, with the holder receiving the specimen container set therein when the holder is drawn out of the main body and being pushed into and set in the main body so that a specimen can be injected by the specimen injecting unit and thus a measurement for a specimen in the second specimen storage unit can be made interruptedly during measurements for specimens in the specimen storage unit are being normally conducted.

8. An automatic analyzer comprising:
a reaction container for having a plurality of disposable reaction vessels set therein;
a reagent injecting unit for injecting a reagent into the disposable reaction vessel;
a specimen injecting unit for injecting a specimen into the disposable reaction vessel;
an absorbance measuring unit for emitting light to the disposable reaction vessel and measuring reaction absorbance of the disposable reaction vessel having a reagent and a specimen injected therein and reacted with each other, and also measures a first blank value representing absorbance of the disposable reaction vessel which is empty and a second blank value representing absorbance of the reaction vessel having only a reagent injected thereinto, wherein the absorbance measuring unit is provided with a designation unit to designate one of the first blank value and the second blank value to be used as a blank value;
an arithmetic unit for calculating based on outputs of the absorbance measuring unit compensating the reaction absorbance based on the blank value; and
a controller for controlling the absorbance measuring unit.

\* \* \* \* \*